United States Patent [19]

Kragen

[11] 4,052,264

[45] Oct. 4, 1977

[54] AGAR-BASE GELLING PRODUCTS

[75] Inventor: Horst Kragen, Velizy Villacoublay, Yvelines, France

[73] Assignee: Ceca S.A., Yvelines, France

[21] Appl. No.: 663,494

[22] Filed: Mar. 3, 1976

[30] Foreign Application Priority Data

Mar. 4, 1975 France .............................. 75.06734
Dec. 29, 1975 France .............................. 75.39975

[51] Int. Cl.² ............................................... C12K 1/10
[52] U.S. Cl. ..................................... 195/100; 195/101
[58] Field of Search ................ 195/100, 101, 102, 103

[56] References Cited

PUBLICATIONS

Chemical Abstracts, vol. 70, 100003s; 1969.
Chemical Abstracts, vol. 68, 47308a; 1968.

Primary Examiner—Alvin E. Tanenholtz
Assistant Examiner—Robert J. Warden
Attorney, Agent, or Firm—Fleit & Jacobson

[57] ABSTRACT

Application for bacteriological use, by way of gel supports for culture media, of products consisting of a compound of agar and galactomannane, the proportion of galactomannane representing up to 40%.

9 Claims, 2 Drawing Figures

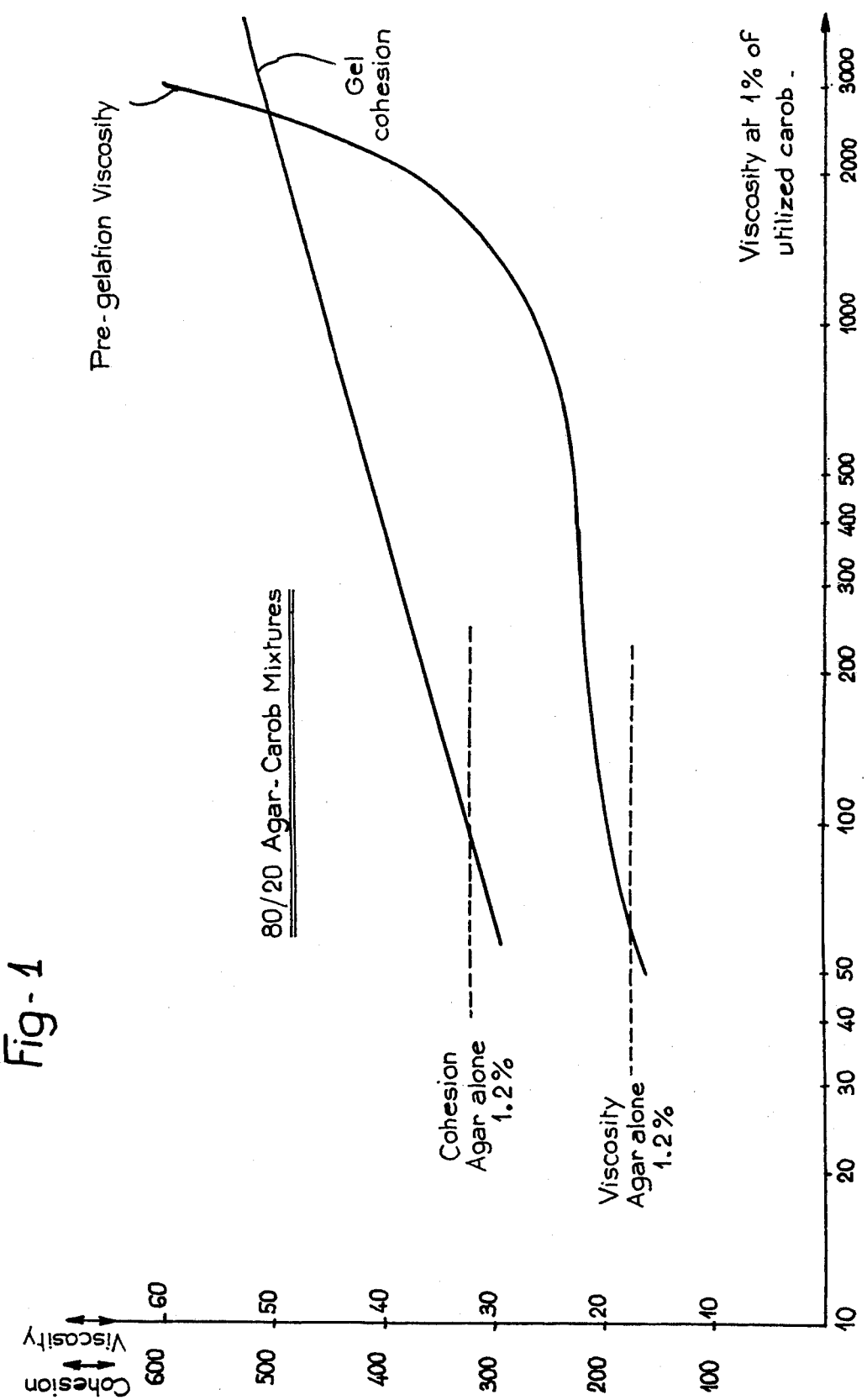

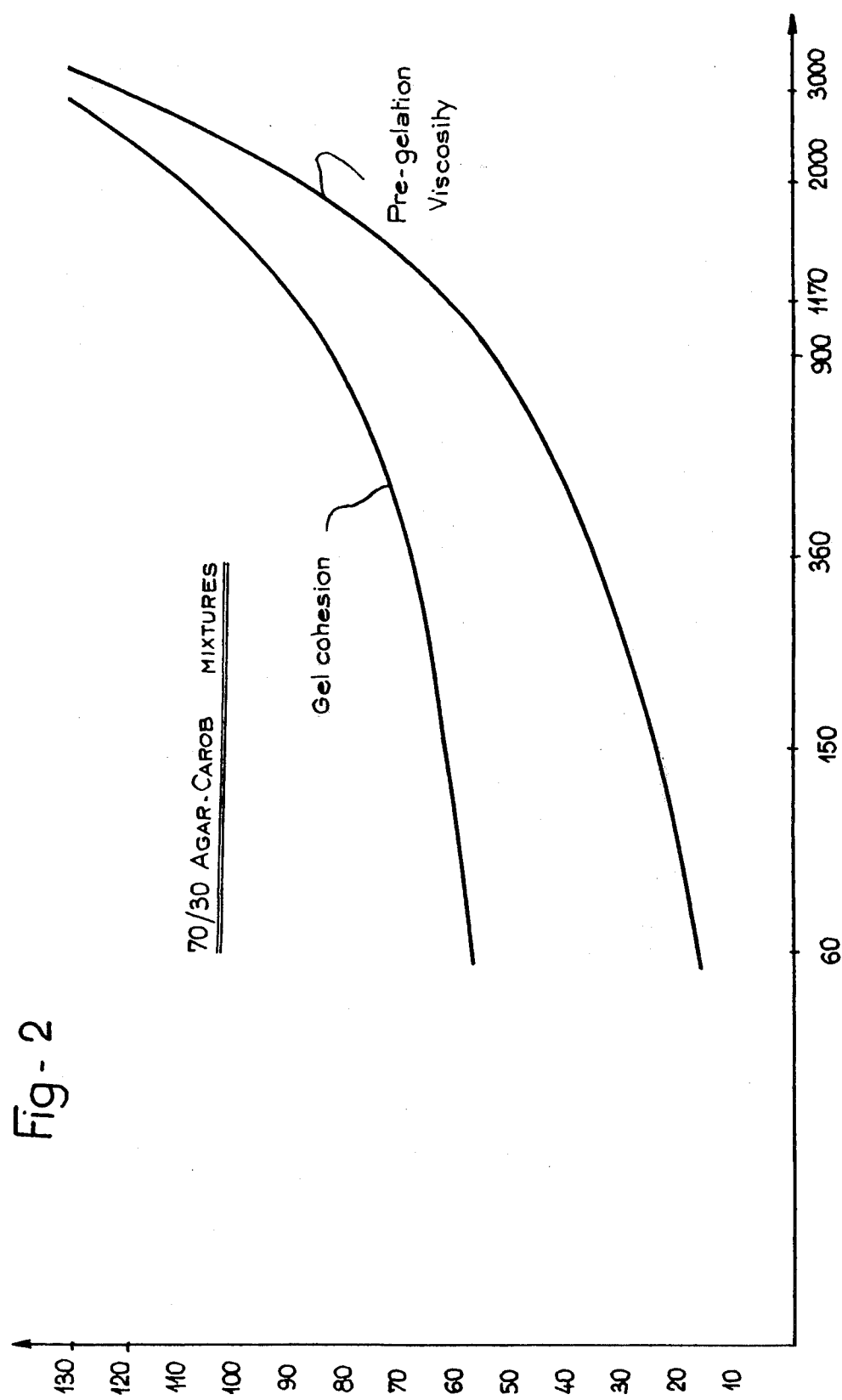

AGAR-BASE GELLING PRODUCTS

The present invention relates in general to agar-base gelling products and has specific reference to novel industrial applications of agar-containing gelling mixtures.

It is known to control the technical behaviour of certain industrial gels obtained from red seaweeds, such as carragheenane or furcellarane, or by microbial synthesis, such as xanthane, by introducing a galactomannane therein.

It is also known that galactomannanes are polysaccharide substances that can be extracted from the seeds of leguminous plants such as: Espina Corona, Tara, Delonix Regia, Carob, Ceratonia Siliqua, Gleditsia-Triacanthos, etc. Galactomannanes obtained from these seeds are in the form of aqueous extracts or meals that can be used as thickening agents and also for forming gels in an aqueous medium.

It has been ascertained that these substances consist (except for some impurities such as proteins, fatty substances, hemicelluloses etc.) only of mannose and galactose, the galactose content varying from 10 to 50% as follows:

|  | Mannose | Galactose |
|---|---|---|
| Carob | 80% | 20% |
| Tara | 78% | 22% |
| Espina Corona | 70% | 30% |
| Guar | 60% | 40% |

Various studies proved that these substances could be designated by a developed formula comprising a main chain of D-mannose bonded at $\beta$ (1 → 4) from which D-galactose bonded at $\alpha$ (1 → 6) are branched, the formula having the following pattern:

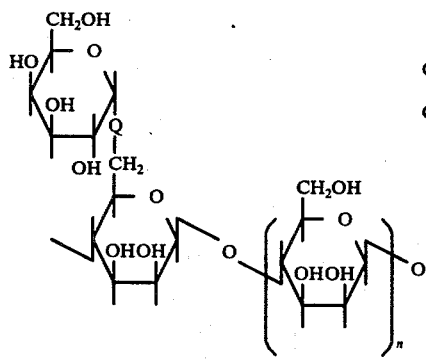

Guar n = 1

Carob n = 3

More particularly, the present invention is directed to the use, as a gelling agent for a bacteriological culture medium, of a galactomannane in admixture with the gel known under the name of agar (or agar-agar) and obtained mainly from red seaweeds.

Agar comprises essentially two different fractions:
  agarose, a neutral polysaccharide, and
  agaropectine, a polysaccharide characterised by the sulfate group.

It is used chiefly in bacteriology as a gelling agent for culture media. To this end, nutritive substances are incorporated in the support, and the whole is sterilized at a relatively high temperature, whereafter it is partially cooled and eventually poured into a starilized petri box and seeded, before the gelling process begins, with the microorganisms to be identified.

The bacteriological support should display the following properties:
  High gelling capacity,
  Transparency in liquid solution form,
  Minimum $SO_4$ content,
  Capacity of preserving its liquid state at 42° C (seeding temperature) to permit a uniform distribution of the germs,
  Solid state at 37° C (incubation temperature), and
  Good resistance to bacterial attacks.

The inventor actually found that one fraction of the agar may be replaced with galactomannane in proportions of up to 80%, this substitution, up to 40%, being free of any fundamental changes in the gel behaviour, such as solubilisation temperature, gelling, behaviour during the incubation, viscosity; however and in addition, this substitution is attended by important improvements notably in the gel transparency, giving an equal thickness and a reduction in the $SO_4$ ions content.

More particularly:
  assuming a 25% thickness increment, the 80/20 agar and carob extract has the same transparency as pure agar,
  assuming a 50% thickness increment, the 60/40 agar and carob extract has the same transparency as pure agar.

On the other hand, for bacteriological applications, the presence of sulfate ions in the agar gel is highly objectionable and it is for this specific reason that up to now agarose and agaropectine had to be separated from each other under very expensive operating conditions.

The addition of a neutral gum to agar reduces the final $SO_4$ ions content in the agaropectine, whereby agar can be utilized in its normal form without having to separate said agaropectine beforehand.

The strength of the compound gel obtained according to this invention may be measured by means of the Bloom gelometer, the figure thus obtained corresponding to the weight necessary for sinking the 12.5 mm diameter piston to a depth of 4 mm into the gel.

| Gelling agents (%) | Gel strength (grams) |
|---|---|
| Agar 1% | 400 |
| Agar 0.8% + 0.2% carob | 450 |
| Agarose 1% | 670 |
| Agarose 0.8% + carob 0.2% | 800 |

Finally, a specific advantage deriving from the partial replacement of agar with galactomannane is the considerable reduction of the gel cost, considering the cost of agar.

Laboratory tests proved that the desired improvements, such as higher gel strength, improved transparency of both solutions and gels, lower ionic charge concentration, could be obtained with a sharpness increasing when galactomannane-bearing purified extracts of seeds, carob or the like, are used. However, these purified extracts yield high-viscosity liquids when dissolved in water.

It should be noted that in the following disclosure the term "carob extract" is used for the sake of simplification, for similar or identical results may be obtained by using extracts from other galactomannane-bearing plants, notably those mentioned hereinabove and more particularly tara seeds and Espina Corona seeds.

In certain bacteriological applications, an excessive viscosity of the agar + carob extract compound before gelation is detrimental to a homogeneous distribution of the bacteria for operators accustomed to treat agar separately, which yields low-viscosity solutions.

According to a specific feature characterizing this invention, it is possible to remedy this high-viscosity inconvenience while preserving the above-mentioned advantages.

In fact, by resorting to a controlled depolymerisation it is possible to obtain carob extracts having a considerably variable degree of polymerization leading to aqueous solutions the viscosity of which decreases with the degree of polymerization.

It was observed that when these depolymerized carob extracts are used with agar for obtaining gelling compounds, the gel strength varies according to the degree of polymerization of the carob extract implemented, and that, except for deeply polymerized carob extracts, the results obtained with agar alone are improved appreciably while preserving the above-specified advantages.

The terms "depolymerized carob" or "depolymerized carob meal" designate herein products of which the degree of polymerization is reduced through physical, chemical or biochemical processes, whereas products having a low degree of polymerization may under certain conditions be obtained naturally (for example as a consequence of bad weather conditions or a late crop).

Physical processes consist essentially in treating the substance by crushing, applying ultrasonic energy, or like means.

Chemical processes include the use of oxidizing or acid degradations, by operating either in suspension or in the dry state.

Biochemical process involve an enzymatic degradation capable of cutting preferentially the glycosidic bonds of the carob polysaccharide.

The depolymerization of a carob extract in acid medium and in suspension in an alcohol medium, respectively, will now be described by way of example:

100 Grams of carob extract are held in suspension while stirring in two litres of isopropyl alcohol. This suspension is maintained under backflow conditions and acidified by using HCl (N). Then the reflux is maintained during variable time periods. Finally, the product is neutralized, and the carob extract is removed and washed with claim clean isopropyl alcohol.

The following Table I illustrates the various viscosities of depolymerized 1% carob extract, according to the degree of depolymerization.

TABLE I

| Heating time mn HCl (N) (c.c.) | 0 | 7 | 10 | 15 | 20 | 25 | 30 |
|---|---|---|---|---|---|---|---|
| 0 | 2800 cps | | | | | | |
| 8 | | | | 950 cps | | | |
| 10 | | 1100 cps | 750 cps | 300 cps | 270 cps | 180 cps | 55 – 70 70 – 70 cps |
| 15 | | | | 125 cps | 60 – 80 cps | | |

The viscosities mentioned hereinabove and in the following disclosure are expressed in centipoises by measuring at 25° C at 20 r.p.m. with a Type RVT Brookfield viscosimeter over a 1-percent carob solution completely by heating to 90° C.

EXAMPLE 1

Determination of viscosity and gel strength values in the culture media with 80/20 agar-carob mixtures.

A comparison was made between two solutions: a 1.2-percent agar solution and a solution containing 1.2-percent of a mixture of agar (80%) and carob extract (20%). The viscosity of these solutions was tested for decreasing rates of polymerization, at 43° C, before the gelation occurred. Then the gel cohesion (i.e. the force necessary for sinking a 1.2 cm diameter piston through 4 mm of gel) was measured. The results are shown in the following Table II.

TABLE II

| | Solution containing 1.2% of agar (80%) and carob (20%) in water | |
|---|---|---|
| Carob at various degrees of polymerization expressed by the viscosity at 1% | Viscosity at 43° C before gelation cps | Gel cohesion (g) |
| 3000 | 60 | 535 |
| 2000 | 37 | 480 |
| 1170 | 27.5 | 465 |
| 900 | 25 | 450 |
| 360 | 22.5 | 380 |
| 150 | 21 | 360 |
| 60 | 17.5 | 290 |
| Agar alone at 1.2% | 17.5 | 320 |

The corresponding curves are illustrated in the accompanying FIG. 1.

From the above Table II and the curves of FIG. 1, it is clear that even when strongly depolymerized the carob extract substituted for 20% of agar will reinforce the agar gel, except for the carob extract having a viscosity of 60 cps at 1%.

It will also be noted that the viscosity of gel compounds before they set to their actual gel state does not increase appreciably as long as the viscosity of the carob extract utilized is less than 1,000 cps at 1%.

Since higher gel strength values are obtained with agar-carob mixtures, it is possible to use less then 1.2% of gelling substance, for example in the case of a 900-cps carob it is only necessary to use 0.9% of gelling compound and in this case the same gel cohesion as in the case of agar alone (at 1.2%) and a 22cps viscosity is obtained.

EXAMPLE 2

Viscosity and strength of gel for culture media with 70-agar and 30-carob extract media, the results being shown in the following Table III.

TABLE III

| | Solution containing 1.2% agar (70%) and carob (30%) in water | |
|---|---|---|
| Carob extract utilized Viscosity at 1% | Viscosity at 43° C | Gel cohesion (g) |
| 3000 | 130 | 640 |
| 2000 | 77 | 560 |
| 1170 | 65 | 500 |
| 900 | 50 | 390 |
| 360 | 37.5 | 340 |
| 150 | 23 | 320 |
| 60 | 17.5 | 260 |

The corresponding curves are illustrated in the accompanying FIG. 2.

It is clear that to combine a low viscosity at 43° C with a satisfactory gel strength, the carob extract utilized should be so depolymerized that its viscosity ranges between 150 and 350 cps.

What is claimed is:

1. A bacteriological culture medium containing agar and galactomannane as gelling agents, said galactomannane being present in an amount effective to gel the medium up to 40% of said gelling agents.

2. The culture medium of claim 1 wherein the gelling agents consist essentially of about 80% of agar and about 20% of galactomannane.

3. The culture medium of claim 1 wherein the gelling agents consist essentially of about 70% of agar and about 30% of galactomannane.

4. The culture medium of claim 1 wherein the gelling agents consist essentially of about 60% of agar and about 40% of galactomannane.

5. The culture medium of claim 1 wherein the galactomannane is depolymerized to the point whereby a 1% solution thereof has a viscosity of less than about 1000 centipoises.

6. The culture medium of claim 1 wherein the galactomannane is obtained from the seeds of a leguminous plant selected from the group consisting of Carob, Tara, Espina Corona, Delonix Regia, Ceratonia Siliqua, and Gleditsia-Triacanthos.

7. The culture medium of claim 1 wherein the galactomannane consists of the extract of Carob seeds.

8. The culture medium of claim 1 wherein the galactomannane consists of the extracts of Tara seeds.

9. The culture medium of claim 1 wherein the galactomannane consists of the extract of Espina Coroma seeds.

* * * * *